(12) United States Patent
Castellani et al.

(10) Patent No.: US 7,504,549 B2
(45) Date of Patent: Mar. 17, 2009

(54) CHEST WOUND SEAL FOR PREVENTING PNEUMOTHORAX AND INCLUDING MEANS FOR RELIEVING A TENSION PHEUMOTHORAX

(75) Inventors: Robert Castellani, Simpsonville, SC (US); Robert Miller, Simpsonville, SC (US)

(73) Assignee: Noth American Rescue Products, Inc., Greer, SC (US)

(*) Notice: Subject to any disclaimer, the term of this patent is extended or adjusted under 35 U.S.C. 154(b) by 219 days.

(21) Appl. No.: 11/232,325

(22) Filed: Sep. 21, 2005

(65) Prior Publication Data

US 2007/0232978 A1 Oct. 4, 2007

(51) Int. Cl.
*A61F 13/00* (2006.01)
*A61M 1/00* (2006.01)

(52) U.S. Cl. .................... 602/41; 604/122; 128/887

(58) Field of Classification Search ............... 604/122, 604/236, 289, 290, 304, 126; 602/41–59; 128/888, 889, 887; 137/553.21, 533.27, 137/843.15
See application file for complete search history.

(56) References Cited

U.S. PATENT DOCUMENTS

| | | | |
|---|---|---|---|
| 3,642,126 A | 2/1972 | Kurtz | |
| 3,874,387 A | 4/1975 | Barbieri | |
| 4,465,062 A | 8/1984 | Versaggi et al. | |
| 4,579,221 A | 4/1986 | Corella | |
| 4,717,382 A | 1/1988 | Clemens | |
| 4,743,232 A | 5/1988 | Kruger | |
| 5,020,160 A * | 6/1991 | Cano | 2/159 |
| 5,090,406 A | 2/1992 | Gilman | |
| 5,112,618 A * | 5/1992 | Cartmell et al. | 424/443 |
| 5,160,322 A | 11/1992 | Scheremet | |
| 5,195,977 A | 3/1993 | Pollitt | |
| 5,263,922 A | 11/1993 | Sova et al. | |
| 5,431,633 A | 7/1995 | Fury | |
| 5,478,333 A | 12/1995 | Asherman, Jr. | |
| 5,662,598 A | 9/1997 | Tobin | |
| 5,951,505 A * | 9/1999 | Gilman et al. | 602/41 |
| 5,998,694 A | 12/1999 | Jensen et al. | |
| 6,099,509 A * | 8/2000 | Brown et al. | 604/180 |
| 6,855,135 B2 * | 2/2005 | Lockwood et al. | 604/313 |

(Continued)

OTHER PUBLICATIONS

Int'l Search Report, Aug. 2, 2007, North American Rescue.

(Continued)

*Primary Examiner*—Kim M Lewis
(74) *Attorney, Agent, or Firm*—McNair Law Firm, P.A.; Seann P. Lahey

(57) ABSTRACT

A flexible sheet having an adhesive layer carried on a bottom side. A collection chamber formed in the adhesive layer by the exclusion of adhesive from a central area of the sheet for receiving fluid from the wound. A drainage channel formed in the adhesive layer by the exclusion of adhesive from a selected area of the sheet extending radially outward from the collection chamber to a drain outlet at a peripheral edge of the sheet to drain fluid from the collection chamber. The collection chamber and drainage channel having an open position allowing fluid to flow outward from the collection chamber through the drain outlet, and a closed position collapsed against the skin to prevent fluid intake through the drain outlet. A storage compartment carried by the flexible sheet including a needle and catheter for immediate access in treating a tension pneumothorax.

19 Claims, 4 Drawing Sheets

U.S. PATENT DOCUMENTS

| | | | |
|---|---|---|---|
| 7,129,389 B1 * | 10/2006 | Watson | 602/48 |
| 7,195,624 B2 * | 3/2007 | Lockwood et al. | 604/543 |
| 2002/0082540 A1 | 6/2002 | Johnston et al. | |
| 2003/0153860 A1 | 8/2003 | Nielsen et al. | |
| 2004/0168944 A1 | 9/2004 | Massengale et al. | |
| 2005/0004501 A1 | 1/2005 | Lorenzo | |
| 2005/0147656 A1 | 7/2005 | McCarthy et al. | |
| 2005/0228331 A1 * | 10/2005 | Tseng et al. | 602/58 |
| 2007/0244421 A1 * | 10/2007 | Graham | 602/43 |

OTHER PUBLICATIONS

Written Opinion, Aug. 2, 2007, North American Rescue.

* cited by examiner

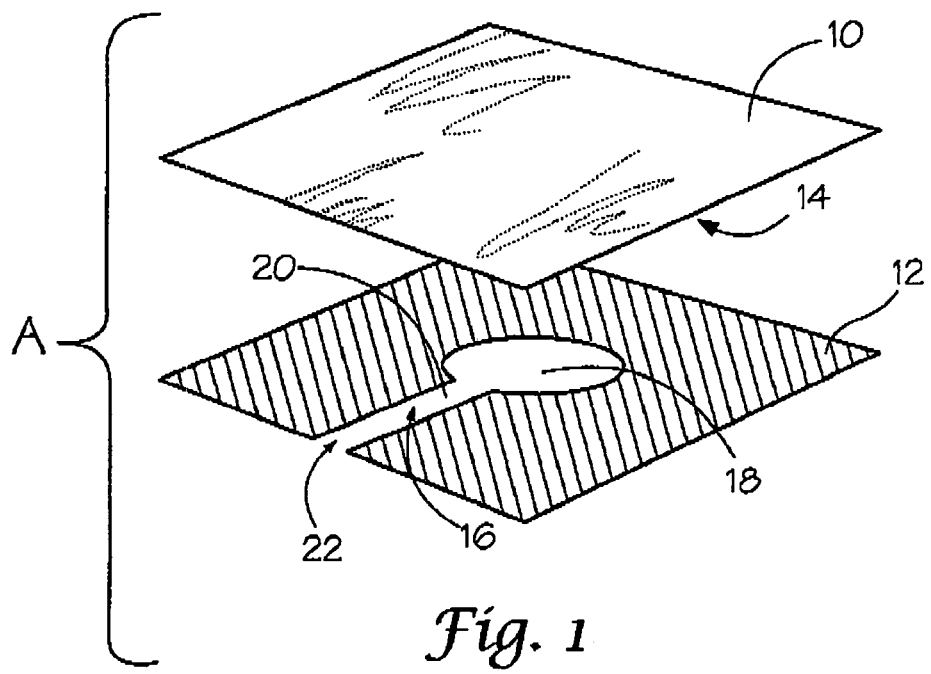
*Fig. 1*
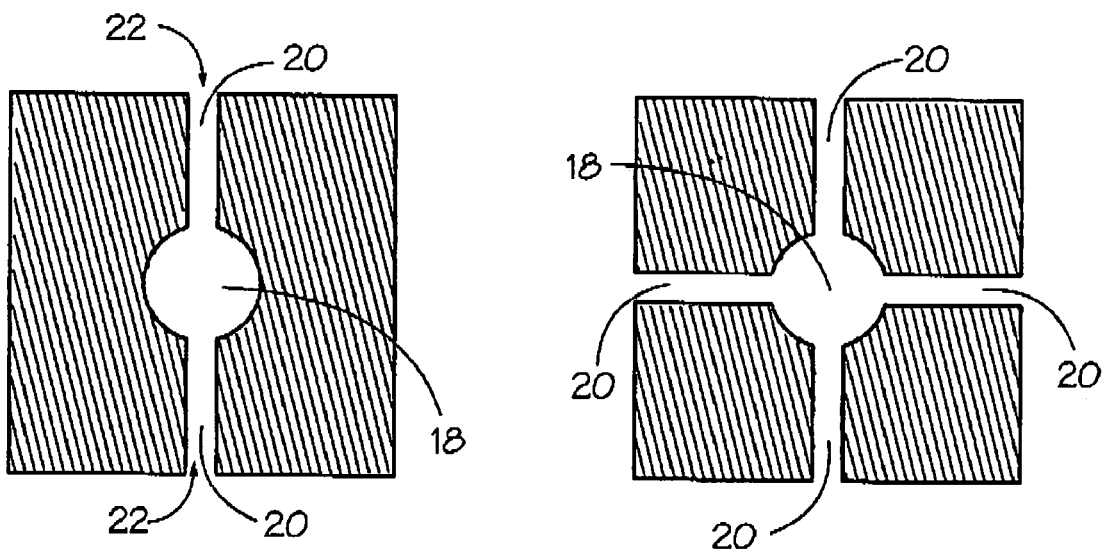
*Fig. 2a*  *Fig. 2b*

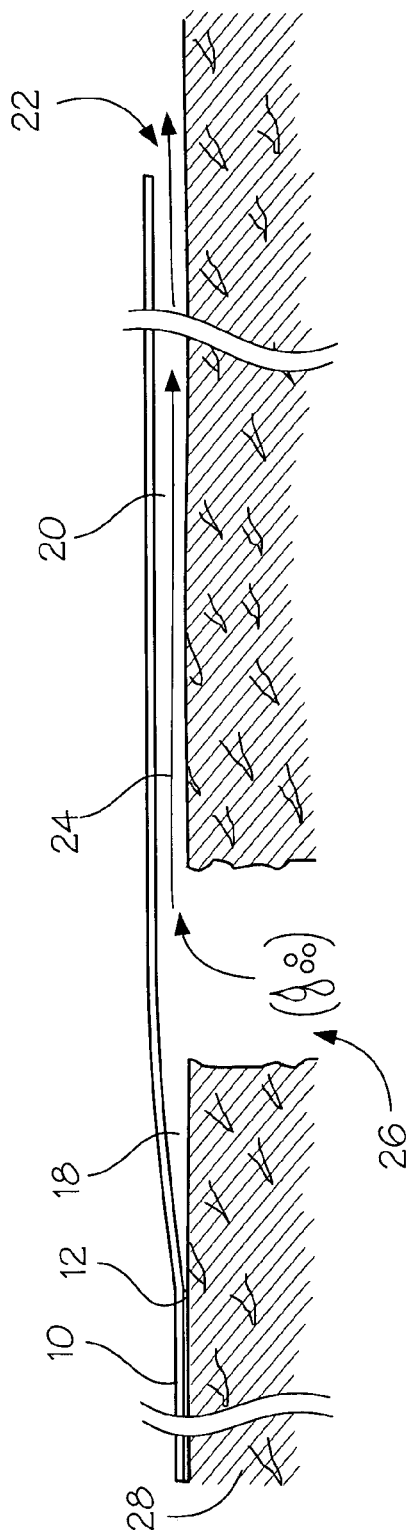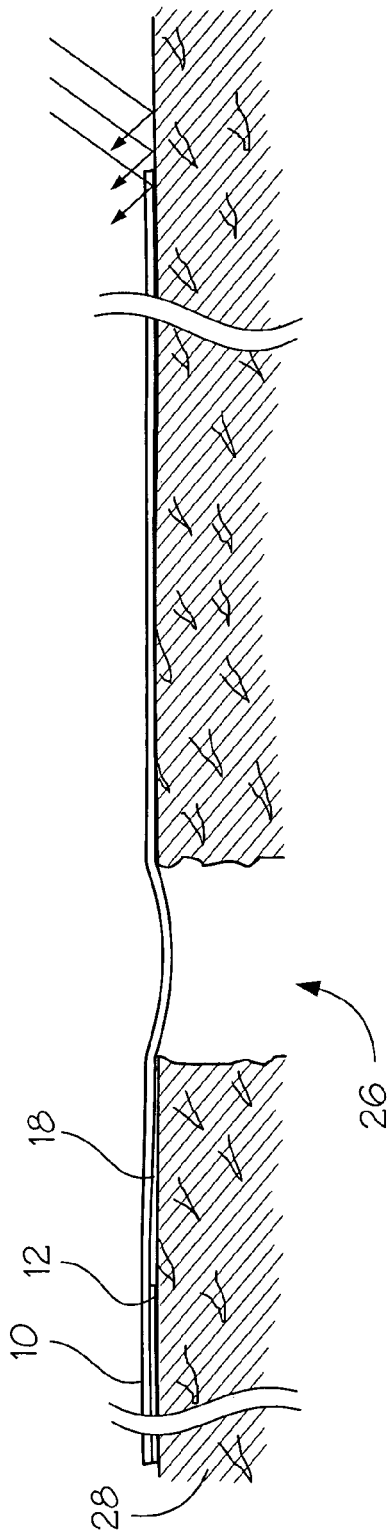

CHEST WOUND SEAL FOR PREVENTING PNEUMOTHORAX AND INCLUDING MEANS FOR RELIEVING A TENSION PNEUMOTHORAX

BACKGROUND OF THE INVENTION

1) Field of the Invention

The present invention relates generally to a dressing for treating a penetrating chest wound, and more particularly, to an occlusive dressing that seals tightly over the would and has a fluid drainage system allowing fluid to exit from the wound while preventing fluid intake, and which carries a needle and catheter for immediate access and use in relieving a tension pneumothorax.

2) Description of Related Art

When a penetrating chest wound occurs, the negative pressure within the pleural space that prevents the lungs from collapsing during normal breathing can be disrupted, resulting in a life threatening situation. The flow of air and other fluids through the wound into the chest cavity can significantly reduce or eliminate this negative pressure. Once this occurs, the lungs lose the ability to inflate. This condition is referred to as a pneumothorax, where air can both enter and exit from the pleural space through the wound, making breathing extremely difficult. Certain penetrating chest wounds, known as a tension pneumothorax, occur when a one-way valve is formed by the wound that allows airflow into the pleural space while preventing airflow out. In a tension pneumothorax, each inhalation traps air in the chest, increasing pressure on the lungs and ultimately causing them to collapse. Additionally, the increasing pressure pushes important structures in the center of the chest, such as the heart, major blood vessels, and airways, towards the sides of the chest. This shifting can cause further compression of the lungs and may affect the flow of blood returning to the heart. These additional complications in a tension pneumothorax make it a life threatening condition that requires immediate treatment.

The prior art includes various dressings designed to prevent the intake of fluid into the chest cavity for penetrating chest wounds. However, these dressings are designed for civilian emergency medical services and were never intended for use under battlefield conditions. Common failures of these devices during combat conditions range from inadequate adhesive for attaching to the skin, insufficient size for covering exit wounds from high velocity projectiles, difficult access to the product due to packaging, and extended time being required to apply the dressing. Also, not a single dressing in the prior art attempts to address the issue of relieving a tension pneumothorax by providing the means for treating the condition in a convenient and immediately accessible package together with the dressing.

For example, U.S. Pat. No. 5,160,322 is representative of a plurality of similar type dressing which disclose an occlusive chest sealing valve that includes a plastic sheet carrying a check valve that allows fluid to exit the wound and pass through the valve but prevents fluid intake in order to maintain the negative pressure within the pleural space. A problem with this design, however, is that dirt and other debris may find its way into the valve assembly and prevent proper operation. Additionally, the adhesive used on these plastic sheet type dressings fails under the rigors of combat conditions and the dressing becomes dislodges. Also, the plastic sheet is not sufficiently flexible to adapt to the various contours of the chest to provide a sufficient seal for any extended period of time, or which can be reapplied. Further, the valve assembly increases the cost of the dressing.

U.S. Pat. No. 5,662,598, discloses another dressing for a penetrating chest wound. This design uses a gauze pad as a buffer between the skin and a flexible plastic sheet which blocks airflow into the wound. One portion of the sheet adjacent the gauze pad does not include any adhesive to allow fluid to exit from under the sheet. The gauze pad is impregnated with silicone, adding significant cost to the dressing. Further, if the non-adhesive flap portion of the dressing becomes distorted in laying flat against the skin, the dressing becomes ineffective at preventing fluid intake. Also, because of the size of the gauze pad under the sheet, there is only a small amount of adhesive for holding the dressing in place, and may be easily dislodged.

Additionally, as noted above, none of the prior art patents teach any means in association with the dressing for relieving excess pressure which may have already built up in the pleural space.

Accordingly, it is an object of the present invention to provide a dressing for a penetrating chest wound that is capable of maintaining an effective seal over the wound which blocks fluid intake while allowing fluid outflow despite exposure to dirt and debris and jostling of the patient under the extreme rigors of combat conditions.

It is a further object of the present invention to provide a dressing for a penetrating chest wound that is simple to manufacture, is easy to apply over the wound, and is lower in cost to manufacture than the dressings taught in the prior art.

It is a further object of the present invention to provide a dressing for a penetrating chest wound that includes means for relieving excess pressure that is trapped and has accumulated in the pleural space.

SUMMARY OF THE INVENTION

The above objectives are accomplished according to the present invention by providing an occlusive dressing for a penetrating chest wound comprising a thin flexible sheet with an adhesive layer carried on a bottom side of the sheet for adhering the sheet to skin surrounding the chest wound. A collection chamber is formed in the adhesive layer by the exclusion of adhesive from a generally central area of the sheet for being positioned over the wound to receive fluid from the wound. A drainage channel is formed in the adhesive layer by the exclusion of adhesive from a selected area of the sheet extending radially outward from the collection chamber to a drain outlet at a peripheral edge of the sheet to drain fluid from the collection chamber out from under the sheet.

The collection chamber and drainage channel have an open position allowing fluid to flow outward from the collection chamber through the drain outlet, and a closed position collapsed against the skin to prevent fluid intake through the drain outlet.

The sheet is formed from a generally fluid impermeable plastic, which is preferably clear to allow inspection of the wound through the sheet. In a further advantageous embodiment, the adhesive layer consists of a hydrogel polymeric composition.

In a further advantageous embodiment, a plurality of drainage channels are circumferentially spaced around and radially extending from the collection chamber with each having a first end connected to the collection chamber and a second end connected to a drain outlet at the peripheral edge of the sheet.

In a preferred embodiment, the sheet includes a textured surface grip on a top side of the sheet for providing a non-slip surface to grip when applying to the skin. In one embodiment, the sheet includes a thumb pad extending from a portion of the peripheral edge of the sheet that also includes a textured surface grip for removing an adhesive backing layer from the adhesive layer.

In a most advantageous embodiment, a chest decompression needle and catheter are carried by the sheet for emergency use in venting excess air pressure trapped in the pleural cavity of the chest. In a further embodiment, a storage compartment is detachably carrying the chest decompression needle and catheter along the peripheral edge of the sheet. In an alternative embodiment, the storage compartment is included on the top side of the sheet for storing the chest decompression needle for emergency use.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 1 shows an exploded view of the dressing according to the present invention;

FIGS. 2a and 2b show alternative embodiments of the adhesive layer according to the present invention;

FIG. 5a shows a cross-section view of the dressing in FIG. 4a; and,

FIG. 5b shows a cross-section view of the dressing in FIG. 4b.

DETAILED DESCRIPTION OF A PREFERRED EMBODIMENT

Figure 3A:
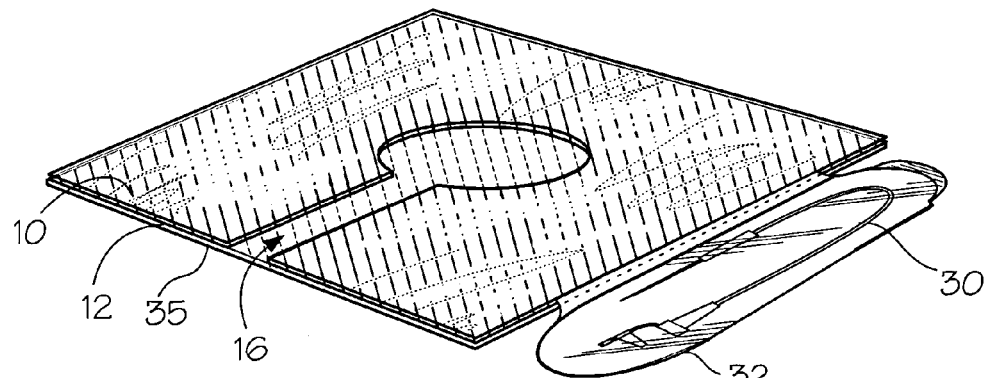
FIGS. 3a and 3b show the dressing carrying a chest decompression needle according to the present invention.

With reference to the drawings, the invention will now be described in more detail. Referring to FIG. 1, an occlusive dressing A for a penetrating chest wound is shown which includes a thin flexible sheet 10, and an adhesive layer 12 carried on a bottom side 14 of the sheet for adhering the sheet to skin surrounding the chest wound. A fluid drain, designated generally as 16, is included in adhesive layer 12 that is defined by an absence of adhesive on selected areas of sheet 10. Sheet 10 Is constructed and arranged to be applied over the wound to position a portion of fluid drain 16 directly over the wound for receiving fluid from the wound and channeling the fluid out from under sheet 10 while also preventing fluid intake into the wound.

In one embodiment, sheet 10 is formed from a generally fluid impermeable plastic in approximately an 8"×8" square. However, the size and shape may be altered to suit particular applications and methods of manufacturing and the invention is not limited to a particular shape or size. The 8"×8" square is more suitable for dealing with the type of large wounds inflicted by high impact projectiles under combat conditions. The preferred size noted above also provides sufficient adhesive area for securely attaching sheet 10 over a wound as well as providing sufficient space for incorporating fluid drain 16 into adhesive layer 12 to control the discharge of fluid while preventing fluid intake. Additionally, sheet 10 is preferably clear to allow inspection of the wound through the sheet. In this embodiment, it is also advantageous to use an adhesive that is also generally clear.

In a preferred embodiment, adhesive layer 12 is provided in the form of a hydrogel polymeric composition. When compared to traditional glue adhesives, hydrogel is a vast improvement. Its chemical structure allow it to mold exactly to body contours to eliminate potential air gaps, while also flexing and stretching with the skin as the body moves without becoming even slightly dislodged. Further, it can be reapplied numerous times without losing its adhesive properties. Hydrogel provides an airtight seal over the wound and has the added benefits of absorbing wound excreta, does not stick to the wound, can be made transparent to allow for monitoring of the wound without removing the seal, is non-antigenic and non-allergenic, and is easy to store and apply.

Referring to FIGS. 1, 2a, and 2b, fluid drain 16 includes a collection chamber 18 formed in adhesive layer 12 by the exclusion of adhesive from a generally central area of the sheet for being positioned over the wound to receive fluid from the wound. A drainage channel 20 is formed in the adhesive layer by the exclusion of adhesive from a selected area of the sheet extending radially outward from the collection chamber to a drain outlet 22 at a peripheral edge of sheet 10 to drain fluid from collection chamber 18 out from under sheet 10. In an alternative embodiment, a plurality of drainage channels 20 can be formed in adhesive layer 12 to deal with larger amounts of fluid evacuation. As shown in FIGS. 2a and 2b, drainage channels 20 are circumferentially spaced around and radially extending from collection chamber 18 with each having a first end connected to collection chamber 18 and a second end connected to drain outlet 22 at the peripheral edge of sheet 10. Using the 8"×8" sheet noted above, in a preferred embodiment, collection chamber 18 is approximately 2" in diameter and located centrally on sheet 10. Additionally, it is preferred that drainage channels 20 be approximately ½" wide to provide sufficient fluid drainage from collection chamber 18. It should be noted that the width of drainage channel 20 can be reduced when using multiple drainage channels, but to provide the most efficient drainage, the ½" width is most preferred.

Figure 4A:
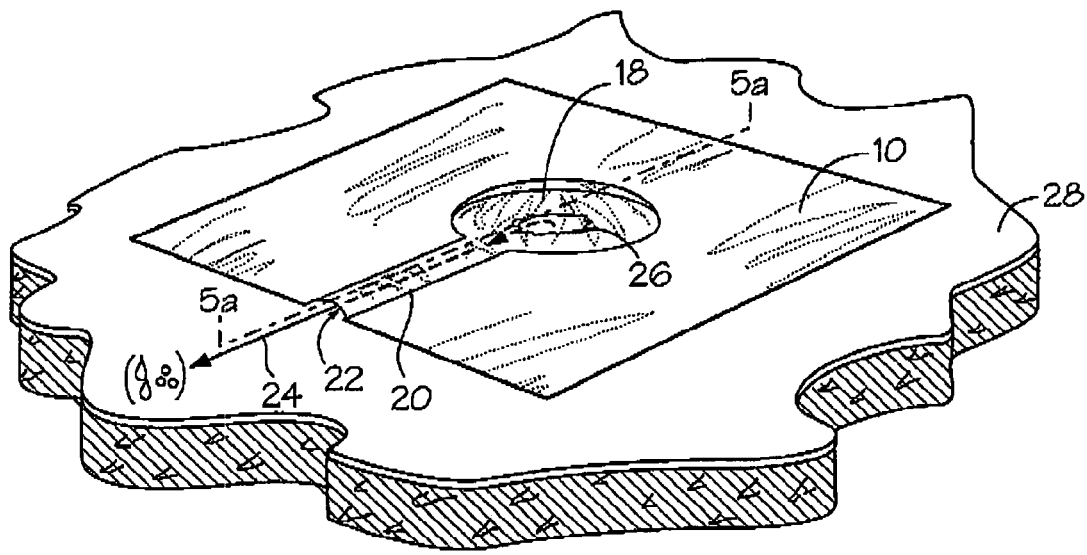
FIG. 4a shows a perspective view of the dressing applied to a chest wound allowing fluid to drain from the wound according to the present invention.

Referring to FIGS. 4a and 5a, collection chamber 18 and drainage channel 20 are shown having an open position allowing fluid, designated by reference arrow 24, to flow outward from collection chamber 18 through drain outlet 22. In the open position, fluid is forced upward from the wound, designated generally as 26, into collection chamber 18, causing the chamber to rise up off of skin 28. The expired fluid flows from collection chamber 18 into drainage channel 20 and out drain outlet 22. As fluid is directed into drainage channel 20, sheet 10 rises off the skin due to the lack of adhesive and fluid 24 is allowed to be expelled from under sheet 10 at drain outlet 22.

Figure 4B:
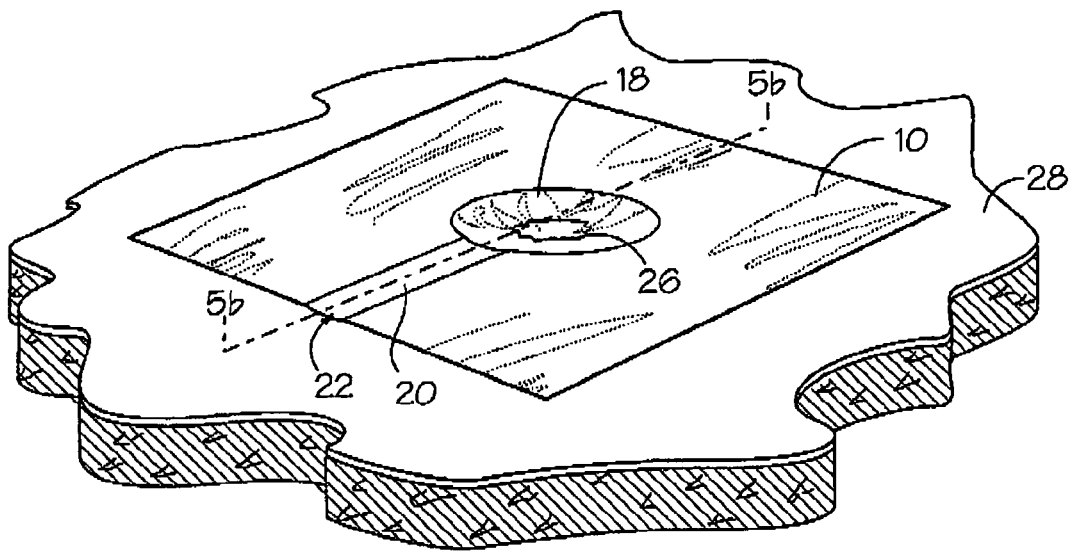
FIG. 4b show a perspective view of the dressing applied to a chest wound preventing the intake of fluid into the wound according to the present invention.

Referring to FIGS. 4b and 5b, collection chamber 18 and drainage channel 20 further have a closed position collapsed against the skin to prevent fluid intake through drain outlet 22 to maintain air pressure levels within the chest cavity and prevent a tension pneumothorax condition from developing. When fluid is not being expelled, the areas of sheet 10 that do not include adhesive layer 12 lay flat against skin 28. The negative pressure within the chest cavity draws collection chamber 18 and drainage channel 20 tight against the skin in a generally air tight arrangement. By collapsing under the negative pressure, sheet 10 blocks the inflow of fluid into the chest cavity and maintains the negative pressure of the chest cavity. Fluid drain 16 is only in the open position when the pressure of fluid being expired from wound 26 exceeds the negative pressure created within the chest cavity.

When using hydrogel for adhesive layer 12, the adhesive layer may be thicker than when using a traditional glue adhesive. Accordingly, in order for fluid drain 16 to function properly when using a thicker hydrogel, sheet 10 needs to be sufficiently flexible to accommodate the thickness of adhesive layer 12 and allow for sheet 10 to collapse against the skin under the negative pressure of the chest cavity. In a preferred embodiment, sheet 10 may be comprised of a polyethylene film. Alternatively, fluid drain 16 may be entirely removed to provide a continuous layer of hydrogel completely sealing off the wound area. This embodiment is an effective temporary solution when dealing with an uncomplicated pneumothorax. In the event of a tension pneumothorax, the presence of fluid drain 16 is less important due to the fact that air is already trapped in the pleural space. In this situation, the primary importance is to immediately relieve the excess pressure which has accumulated in the pleural space. Thus, while the dressing described above will prevent any further increase in pressure and even allow some fluid to escape the chest cavity, it will not treat a tension pneumothorax. The currently preferred method for treating tension pneumothorax under combat conditions for stabilizing the patient for emergency evacuation is needle decompression. This involves inserting a large-bore 14-16 gauge needle with a catheter into the second intercostal space. Once the needle is in the pleural space, the air escapes through the catheter which remains in place while the needle is removed.

Figure 3B:
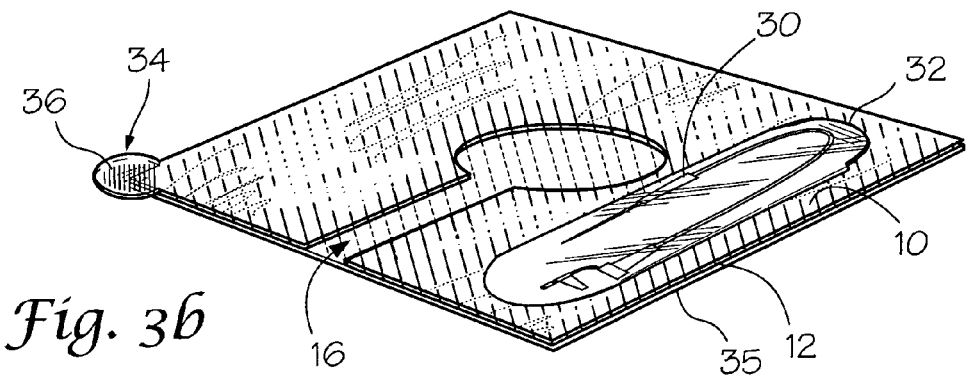

Accordingly, referring to FIGS. 3a and 3b, an alternative embodiment is shown wherein a chest decompression needle and catheter 30 is carried by sheet 10 for emergency use in venting excess air pressure trapped in the pleural cavity of the chest to relieve a tension pneumothorax. By including chest decompression needle and catheter 30 on sheet 10, a complete solution is provided for dealing with penetrating chest wounds. As shown in FIG. 3a, in the preferred embodiment, a needle compartment 32 is detachably carrying chest decompression needle and catheter 30 along the peripheral edge of sheet 10. Needle storage compartment 32 is preferably of a perforated tear-off type compartment that can be easily detached for use or to be discarded if not needed. As shown in FIG. 3b, needle storage compartment 32 is included on a top side of sheet 10 for storing the chest decompression needle for emergency use. In this embodiment, storage compartment 32 may be soft glued to the top of sheet 10, or may be integrally formed as part of sheet 10. Although conveniently located, this embodiment can limit the flexibility of sheet 10 if needle 30 is not removed once sheet 10 has been applied to the skin. Accordingly, the embodiment shown in FIG. 3a is most preferred.

Figure 3C:
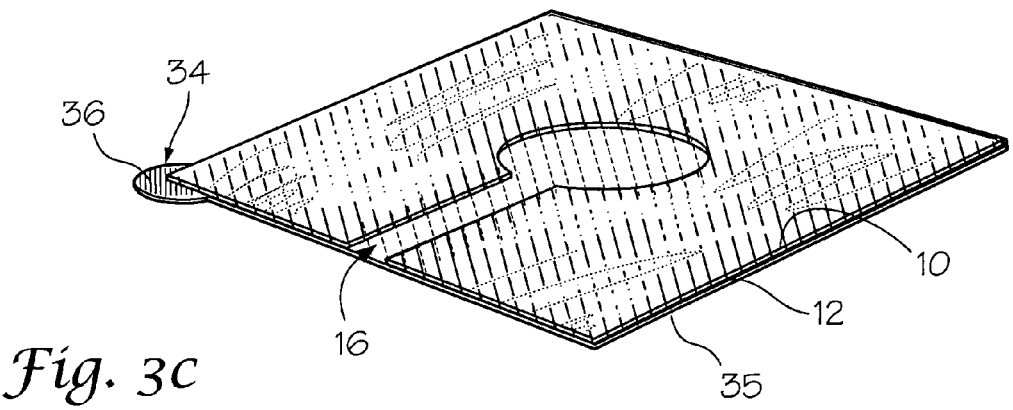
FIG. 3c shows a textured thumb pad included on the dressing according to the present invention.

Referring to FIG. 3b, sheet 10 is constructed and arranged with a textured grip portion on a top side of sheet 10 for providing a non-slip surface to grip the chest seal when applying it over the skin. In a preferred embodiment, sheet 10 includes a thumb pad 36 extending from a portion of the peripheral edge of sheet 10 with textured grip portion 34 located on the thumb pad. This can be used to help remove sheet 10 from an adhesive backing 35 attached to adhesive layer 12 used to protect the adhesive layer for quickly unpackaging the chest seal for application. Alternatively thumb pad 36 with or without textured grip portion 34 may be carried by adhesive backing 35, as shown in FIG. 3c for quick removal of the adhesive backing.

While a preferred embodiment of the invention has been described using specific terms, such description is for illustrative purposes only, and it is to be understood that changes and variations may be made without departing from the spirit or scope of the following claims.

What is claimed is:

1. An occlusive dressing for a chest wound comprising:
a flexible sheet for providing a fluid and debris barrier;
an adhesive layer carried on a bottom side of said sheet for adhering said sheet to skin surrounding the chest wound;
a collection chamber included in said adhesive layer defined by the complete exclusion of adhesive from a generally central area of said sheet for being positioned over the wound to receive fluid from the wound; and,
a drainage channel included in said adhesive layer defined by the complete exclusion of adhesive from a selected area of said sheet extending radially outward from said collection chamber to a drain outlet at a peripheral edge of said sheet to drain fluid from said collection chamber out from under said sheet;
wherein said collection chamber and drainage channel are operable between an open position allowing fluid to flow outward from said collection chamber through said drain outlet, and a closed position with said sheet collapsed against the skin to prevent fluid intake through said drain outlet to prevent fluid from building pressure within the chest cavity.

2. The dressing of claim 1 wherein said sheet is formed from a generally fluid impermeable plastic.

3. The dressing of claim 2 wherein said sheet is clear to allow inspection of said wound through said sheet.

4. The dressing of claim 1 wherein said adhesive layer consists of a hydrogel polymeric composition.

5. The dressing of claim 1 including a plurality of drainage channels circumferentially spaced around and radially extending from said collection chamber with each having a first end connected to said collection chamber and a second end connected to a drain outlet at said peripheral edge of said sheet.

6. The dressing of claim 1 wherein said sheet is constructed and arranged to include a textured surface grip on a top side of said sheet for providing a non-slip surface to grip when applying to the skin.

7. The dressing of claim 1 wherein said sheet includes a thumb pad extending from a portion of said peripheral edge of said sheet and including a textured surface grip for quickly separating said sheet from an adhesive backing layer.

8. The dressing of claim 1 including a chest decompression needle and catheter carried by said sheet for emergency use in venting excess air pressure trapped in the pleural cavity of the chest.

9. The dressing of claim 8 including a storage compartment detachably carrying said chest decompression needle and catheter along said peripheral edge of said sheet 10. The dressing of claim 8 including a storage compartment included on a top side of said sheet for storing said chest decompresslon needle and catheter for emergency use.

11. An occlusive dressing for a chest wound comprising:
a generally fluid impermeable flexible sheet;
an adhesive layer carried on a bottom side of said sheet for adhering said sheet to skin surrounding the wound; and,
a fluid drain included in said adhesive layer defined by a complete absence of adhesive on selected areas of said sheet;
said fluid drain including a drainage channel defined by the selective exclusion of adhesive on said sheet extending radially outward from said collection chamber to a peripheral edge of said sheet to drain fluid out from under said sheet;

wherein said sheet is constructed and arranged to be applied over the wound to position a portion of said fluid drain directly over the wound for receiving fluid from the wound and channeling the fluid out from under said sheet while preventing fluid intake into the wound.

12. The dressing of claim 11 wherein said fluid drain includes a collection chamber formed in a generally central area of said sheet by the exclusion of adhesive for receiving fluid directly from the wound and channeling said fluid through said drainage channel.

13. The dressing of claim 12 wherein said sheet includes a textured surface grip on a top side of said sheet for providing a non-slip surface to grip when applying to the Skin.

14. The dressing of claim 13 including a detachable storage compartment carried by said sheet including a chest decompression needle and catheter carried in said storage compartment for emergency use in venting excess air pressure trapped in the pleural cavity of the chest.

15. The dressing of claim 14 wherein said adhesive layer consists of a hydrogel polymeric composition.

16. An occlusive dressing for a chest wound comprising:

an adhesive layer consisting of a hydrogel polymeric composition for placement over the wound;

a fluid drain included in said adhesive layer defined by a complete absence of adhesive on selected areas of said sheet;

said fluid drain including a drainage channel defined by the selective exclusion of adhesive on said sheet extending radially outward from said collection chamber to a peripheral edge of said sheet to drain fluid out from under said sheet;

a flexible sheet carried on a top side of said adhesive layer to form a fluid and debris barrier over said adhesive layer;

a storage compartment carried by said flexible sheet;

a needle carried in said storage compartment adapted for penetrating the chest into the pleural space; and, a catheter carried in said storage compartment operatively associated with said needle for allowing air to escape the pleural space and relieve a tension pneumothorax;

whereby a penetrating chest wound causing a tension pneumothorax can be sealed and the air pressure causing the tension pneumothorax in the pleural space relieved.

17. The dressing of claim 16 wherein said storage compartment is detachably carried by said flexible sheet for quick and convenient access to said needle and catheter when treating a tension pneumothorax and allowing said adhesive layer and flexible sheet to conform to body contours.

18. The dressing of claim 16 wherein said needle is an intravenous needle In the range of 14 to 16 gauge and at least 3cm long.

19. The dressing of claim 16 wherein said flexible sheet includes a textured surface for gripping said sheet to apply said adhesive layer to the skin.

* * * * *

UNITED STATES PATENT AND TRADEMARK OFFICE
CERTIFICATE OF CORRECTION

PATENT NO. : 7,504,549 B2
APPLICATION NO. : 11/232325
DATED : March 17, 2009
INVENTOR(S) : Robert Castellani and Robert Miller Page 1 of 1

It is certified that error appears in the above-identified patent and that said Letters Patent is hereby corrected as shown below:

Title Page, Item (54) Title: the word "PHEUMOTHORAX" should read "PNEUMOTHORAX".

Signed and Sealed this

Second Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,504,549 B2 Page 1 of 1
APPLICATION NO. : 11/232325
DATED : March 17, 2009
INVENTOR(S) : Robert Castellani and Robert Miller It is certified that error appears in the above-identified patent and that said Letters Patent is hereby corrected as shown below:

Title Page, Item (54) and Column 1, line 4, Title: the word "PHEUMOTHORAX" should read "PNEUMOTHORAX".

This certificate supersedes the Certificate of Correction issued June 2, 2009.

Signed and Sealed this

Twenty-third Day of June, 2009

JOHN DOLL
*Acting Director of the United States Patent and Trademark Office*

UNITED STATES PATENT AND TRADEMARK OFFICE
CERTIFICATE OF CORRECTION

PATENT NO.         : 7,504,549 B2
APPLICATION NO.  : 11/232325
DATED              : March 17, 2009
INVENTOR(S)        : Robert Castellani and Robert Miller It is certified that error appears in the above-identified patent and that said Letters Patent is hereby corrected as shown below:

In claim 11 at column 7, line 1, "said collection chamber" should read --a collection chamber--.

In claim 12 at column 7, line 10, "a collection chamber" should read --said collection chamber--.

Signed and Sealed this

Third Day of November, 2009

David J. Kappos
*Director of the United States Patent and Trademark Office*